United States Patent [19]

Poli et al.

[11] Patent Number: 5,066,644
[45] Date of Patent: Nov. 19, 1991

[54] DERIVATIVES OF THIAZOLIDINE-4-CARBOXYLIC ACID, ITS PREPARATION AND PHARMACEUTICAL COMPOSITIONS CONTAINING IT

[75] Inventors: Stefano Poli; Germano Coppi; Lucio Del Corona, all of Milan, Italy

[73] Assignee: Poli Industria Chimica S.p.A., Milan, Italy

[21] Appl. No.: 477,507

[22] Filed: Feb. 9, 1990

[30] Foreign Application Priority Data

Feb. 10, 1989 [IT] Italy ................ 19401 A/89

[51] Int. Cl.[5] .................. C07K 5/06; A61K 37/02
[52] U.S. Cl. .................................. 514/19; 548/201
[58] Field of Search .................. 548/201; 514/19

[56] References Cited

U.S. PATENT DOCUMENTS

| 4,839,387 | 6/1989 | Poli | 514/19 |
| 4,840,936 | 6/1989 | Della Bella | 514/18 |
| 4,952,596 | 8/1989 | Della Bella | 514/18 |

FOREIGN PATENT DOCUMENTS 254354  1/1988  European Pat. Off. ............ 548/20

OTHER PUBLICATIONS

March, Advanced Organic Chemistry, pp. 348–350 (1985).

*Primary Examiner*—Robert Gerstl
*Attorney, Agent, or Firm*—Griffin Branigan & Butler

[57] ABSTRACT

Ester or amide derivatives of 3-pyroglutamylthiazolidine-4-carboxylic acid exhibit interesting immunostimulating, antitoxic, antiinflammatory, antioxidental, antiageing properties.

7 Claims, No Drawings

DERIVATIVES OF THIAZOLIDINE-4-CARBOXYLIC ACID, ITS PREPARATION AND PHARMACEUTICAL COMPOSITIONS CONTAINING IT

The present invention concerns 3-L-pyroglutamyl-L-thiazolidine-4-carboxylic acid derivatives having formula I

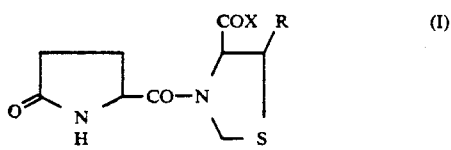

a process for their preparation and pharmaceutical compositions endowed with anti-toxic, anti-oxidant, immunostimulating, antiinflammatory and anti-aging properties.

In formula I X is a $C_1$-$C_7$ alkoxy or aralkoxy group, an amino group, the residue of a $C_1$-$C_8$ primary or secondary aliphatic amine optionally containing one or more double and/or triple bonds, of a primary aralkylamine, of a $C_4$-$C_8$ cyclic aliphatic amine optionally containing an oxygen atom; R is hydrogen or $C_1$-$C_8$ alkyl.

Preferred meanings of X are methoxy, ethoxy, benzyloxy, amino, methylamino, ethylamino, dimethylamino, diethylamino, cyclopropylamino, allylamino, benzylamino, propargylamino, pyrrolidino, piperidino, morpholino.

R is preferably hydrogen or methyl.

EP-A-0276752 discloses 3-pyroglutamyl-L-thiazolidine-4-carboxylic acid and its use as immunostimulant, anti-toxic, anti-oxidant, anti-inflammatory and anti-ageing agent.

It has now been found that the amide and ester derivatives of said acid show improved pharmacological properties.

The compounds of the invention are prepared by usual methods according to scheme A, for instance by reacting the 3-pyroglutamyl-L-thiazolidine-4-carboxylic acid chloride, or activated ester or amide thereof with the suitable alcohols or amines in aprotic solvents and purifying the obtained products by crystallization or by elution on a chromatographic silica column, solvent evaporation and crystallization of the product separated from the original impurities.

SCHEME A

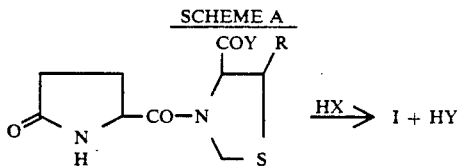

The preferred activated esters are those with hydroxysuccinimide, pentachlorophenol, pentafluorophenol, trichlorophenol, thiophenol, glycolonitrile and the like; preferred amides are those with heterocyclic compounds such as imidazole, pyrazole, 1,2,4-triazole etc.

The compounds I show interesting pharmacological properties combined with an extremely low acute toxicity.

For example, some compounds of the invention have been tested in different immunological tests in comparison with 3-pyroglutamyl-thiazolidine-4-carboxylic acid (PGT).

Since the production of superoxide anion ($O_2^-$) plays an important role in the microbicidal activity of macrophages (N. P. Cumming, M. J. Pabst, J.Exp.Med., 152, 1649, 1980), the showing of a stimulation of the superoxide anion in the macrophages by drugs provides a very important test for the evaluation of immunostimulating activity. The production of $O_2^-$ in peritoneal macrophages isolated from prednisolone immunodepressed animals treated with the compounds of the invention was therefore evaluated. The mice were treated subcutaneously for two days with 0.5 mg/kg/day of prednisolone and with the compounds under examination at the dose of 100 mg/kg twice a day, whereas the morning of the animals sacrifice the animals received the compounds only. The macrophages were then isolated by means of a peritoneal washing and cultured in RPMI-1640 added with 10% foetal calf serum, at the concentration of $1 \times 10^6$ cells/ml at the temperature of $\pm 37°$ C. Amounts of 1 ml of cell suspension were incubated for 15' at 37° C. with horse heart cytochrome C and stimulated with phorbol myristate acetate (H. Nielsen, Eur.J.Clin.Pharmacol., 30, 90, 1986). A specrophotometric determination at $\lambda = 550$ nm of the reduced ferricytochroma using an extinction coefficient $E(550) = 29.5$ mM was then carried out.

As it turns out from Table 1, the prednisolone treatment induces an immunosuppression resulting in a lesser production of superoxide anion; the contemporaneous treatment with the compounds of the invention stimulates the $O_2^-$ production by macrophages up to values close to those of control animals. The compounds have an activity which is from similar to higher than that of PGT at equiponderal doses.

TABLE 1

Activity on the superoxide anion production by peritoneal macrophages from prednisolone-immunodepressed mice

| Treatment | Test n. | nmol cytochrome C reduced/1 × $10^6$ macrophages (mean ± S.E.) |
|---|---|---|
| NaCl 0.9% i.p. | 5 | 11.82 ± 0.61 |
| NaCl 0.9% i.p. + prednisolone 0,5 mg/kg/die/s.c. | 5 | 1.52 ± 0.53 |
| PGT 200 mg/kg/die i.p. + prednisolone 0,5 mg/kg/die/s.c. | 4 | 8.85 ± 0.75** |
| Ia 200 mg/kg/die i.p. + prednisolone 0,5 mg/kg/die/s.c. | 4 | 9.25 ± 0.48** |
| Ib 200 mg/kg/die i.p. + prednisolone 0,5 mg/kg/die/s.c. | 4 | 9.62 ± 0.63** |
| Ic 200 mg/kg/die i.p. + prednisolone 0,5 mg/kg/die/s.c. | 4 | 7.83 ± 0.72** |
| If 200 mg/kg/die i.p. + prednisolone 0,5 mg/kg/die/s.c. | 4 | 7.88 ± 0.82** |
| Ig 200 mg/kg/die i.p. + prednisolone 0,5 mg/kg/die/s.c. | 4 | 8.22 ± 0.61** |
| Ih 200 mg/kg/die i.p. + prednisolone 0,5 mg/kg/die/s.c. | 4 | 9.34 ± 0.47** |
| Il 200 mg/kg/die i.p. + prednisolone 0,5 mg/kg/die/s.c. | 4 | 8.97 ± 0.63** |

**p < 0.01 "t" according to Dunnett vs. immunodepressed control group.

The compounds were tested in endoperitoneal infection in mice. Male COBS CD-1 mice weighing 22-25 g were inoculated i.p. with 0.5 ml/mouse of a pathogenic E.coli suspension (in saline solution + 0.5% porcine gastric mucine), having a transmittance of about 50%. The mice were treated orally with the compounds twice a day from two days before until the day of the infection, 7 hours before the inoculation.

The death-rate was recorded for about 7–8 days after the infection.

The data of Table 2 show that the compounds of the invention have a protective activity against the infection due to a stimulation of the immune system higher than that of PGT after oral administration.

TABLE 2

Activity against E. coli infection in mice

| Treatment | N° dead mice N° treated mice | Protection (%) |
|---|---|---|
| Controls (arabic gum 5%; 10 mg/kg/die os) | 30/30 | 0 |
| PGT 200 mg/kg/die os | 8/10 | 20 |
| Ia 200 mg/kg/die os | 6/10 | 40 |
| Ib 200 mg/kg/die os | 6/10 | 40 |
| Ic 200 mg/kg/die os | 6/10 | 40 |
| If 200 mg/kg/die os | 7/10 | 30 |
| Ig 200 mg/kg/die os | 6/10 | 40 |
| Ih 200 mg/kg/die os | 6/10 | 40 |
| Il 200 mg/kg/die os | 6/10 | 40 |

The compounds proved to be also active in the delayed hypersensitivity induced by dinitrochlorobenzene in prednisolone-immunodepressed mice (A. C. Corsini et al., J.Immunol.Method., 30, 195, 1979).

Male COBS CD-2 mice weighing about 30 g were sensitized with 25 $\mu$l of dinitrochlorobenzene (DNCB) at the concentration of 20 mg/ml in acetone applied on a zone of the abdomen depilated at least 2 hours before.

After 12 hours the animals were challenged with 5 $\mu$l of DNCB at the concentration of 10 mg/ml in acetone applied on the external surface of the left auricolar pinna.

In order to carry out this operation the mice were slightly anesthetized with ether. The mice were treated with the compounds under examination from two days before until the day of sensitization and with the compounds and with prednisolone (0.5 mg/kg/die s.c.; 0.5 ml/10 g) from the tenth day after sensitization until the day when challenge occurred.

The animals were killed 24 hours after the challenge; both ears were cut and weighed. The values are expressed as the ratio between the left ear (sensitized) and the right one (unsensitized). The data of Table 3 show that the treatment with the compounds of the invention increases the delayed hypersensitivity reaction (IV type) in prednisolone-immunodepressed animals. The increase was higher than that obtained after oral administration of PGT.

TABLE 3

Effect on the delayed hypersensitivity by DNCB on prednisolone-immunodepressed mouse

| Treatment | Mouse n. | Weight left ear Weight right ear | Increase % |
|---|---|---|---|
| Controls (arabic gum 5%; 10 ml/kg/die os) | 20 | 1.322 ± 0.025 | — |
| PGT 200 mg/kg/die os | 10 | 1.579 ± 0.027** | 19.44 |
| Ia 200 mg/kg/die os | 10 | 1.688 ± 0.029** | 27.68 |
| Ib 200 mg/kg/die os | 10 | 1.702 ± 0.026** | 28.74 |
| Ic 200 mg/kg/die os | 10 | 1.706 ± 0.028** | 29.05 |
| If 200 mg/kg/die os | 10 | 1.704 ± 0.022** | 28.90 |
| Ig 200 mg/kg/die os | 10 | 1.722 ± 0.023** | 30.26 |
| Ih 200 mg/kg/die os | 10 | 1.639 ± 0.028** | 28.06 |

**$p < 0.01$ "t" according to Dunnett vs. control group.

The compounds of the invention are also active in the test of the rosette forming cells (primary response; II° type) in prednisolone immunodepressed mice (S. D. Wilson, Immunology, 21, 233, 1971).

Male COBS CD-1 mice weighing about 25 g were treated for 7 days twice a day, with the compounds of the invention and at the second and third day with prednisolone at the dose of 5 mg/kg/s.c. (0.05 ml/10 g).

After 4 days from the start of the treatment the 10 animals were immunized with $5 \times 10^8$ sheep red blood cells in 0.2 ml of PBS by intraperitoneal route. The red blood cells were prepared by centrifugating the citrated sheep blood at 1500 rpm for 15 min.; the precipitated red blood cells were washed twice at 1200 rpm for 10 min. in PBS removing the first layer, then suspended again in PBS and counted adjusting at $2.5 \times 10^9$ cells/ml.

After 6 days from the immunization the rosette test was carried out by killing the mice and removing the spleen, which was placed in 1 ml of Hank solution in ice-bath and then triturated, homogenated and gauze-filtered. The homogenate was washed twice in Hank, centrifugating at 1200 rpm for 10 min. and then suspended again. The suspension was adjusted to $6 \times 10^7$ cells/ml by counting at the Coulter Counter after lysis of the red blood cells. 100 $\mu$l of spleen cells suspension $(6 \times 10^7/\text{ml}) + 100$ $\mu$l of red blood cells suspension $(3 \times 10^8/\text{ml})$ were mixed in 0.8 ml of Hank stirring slightly for 1 minute. The samples were incubated for 24 h at $+4°$ C. avoiding any stirring. The samples were then stirred and the number of rosette forming cells/ml was evaluated by means of the Bürker apparatus.

TABLE 4

Action on the rosette forming cells in prednisolone-immunodepressed mice

| Treatment | Mice n. | Rosette forming cells spleen cells % | change % |
|---|---|---|---|
| Control (arabic gum 5%; 10 ml/kg/die os) | 20 | 0.850 ± 0.050 | — |
| PGT 200 mg/kg/die os | 10 | 1.125 ± 0.040** | +32.35 |
| Ia 200 mg/kg/die os | 10 | 1.140 ± 0.032** | +34.12 |
| Ib 200 mg/kg/die os | 10 | 1.138 ± 0.038** | +33.88 |
| Ic 200 mg/kg/die os | 10 | 1.145 ± 0.032** | +34.71 |
| If 200 mg/kg/die os | 10 | 1.138 ± 0.036** | +33.88 |
| Ig 200 mg/kg/die os | 10 | 1.147 ± 0.031** | +34.94 |
| Ih 200 mg/kg/die os | 10 | 1.138 ± 0.043** | +33.88 |

**$p < 0.01$ "t" according to Dunnett vs. control group.

The compounds of the invention have an activity slightly higher than that of PGT.

The compounds of the invention are also active in the test of the activity of the reticulo-endothelial system in the mouse immunodepressed by cyclophosphamide (Biozzi G. et al., Brit. J. Path., 34, 441, 1953). COBS CD-1 mice were injected i.v. with colloidal charcoal (0.32 ml of china ink/ml of saline), 10 $\mu$l of retroorbital blood were then taken out immediately before and after 1, 10 and 20 min. from the intravenous injection, the blood sample was placed in 3 ml of HCl 0.1 N and the absorbance was evaluated at 640 nm and the change of absorbance was evaluated between the time 0 and 20 min. The animals were treated with cyclophosphamide (100 mg/kg i.p.) from the third to the fifth day of treatment and with the compounds under test for 10 consecutive days; the day after the last treatment the test was carried out.

The data of Table 5 show that the treatment with the compounds of the invention increases the activity of the reticulo-endothelial system (disappearance of the colloidal charcoal from the blood) in the mouse immunodepressed by cyclophosphamide in an analogous or higher measure than PGT after intraperitoneal administration.

TABLE 5

Action on the activity of the reticulo-endothelial system in the mouse immunodepressed by cyclophosphamide (means ± SE of 10 mice)

| Treatment | Absorbance$\Delta$ (0'-20') | Variation versus the cyclophosphamide treated group % |
|---|---|---|
| Control (arabic gum 5%; 10 ml/kg/die os) | 0.380 ± 0.020 | — |
| Cyclophosphamide | 0.320 ± 0.015 | — |
| PGT 100 mg/kg/die i.p. | 0.365 ± 0.018** | +14.06 |
| Ia 100 mg/kg/die i.p. | 0.370 ± 0.013** | +15.62 |
| Ib 100 mg/kg/die i.p. | 0.382 ± 0.021** | +19.37 |
| Ic 100 mg/kg/die i.p. | 0.371 ± 0.016** | +15.94 |
| If 100 mg/kg/die i.p. | 0.362 ± 0.011** | +13.12 |
| Ig 100 mg/kg/die i.p. | 0.367 ± 0.012** | +14.69 |
| Ih 100 mg/kg/die i.p. | 0.383 ± 0.041** | +19.69 |

**$p < 0.01$ "t" according to Dunnett vs. cyclophosphamide treated group.

The compounds of the invention had also a comparable or higher activity than PGT in the test of paracetamol intoxication and in the protection from ionizing radiations.

The compounds I are also active in improving the neurocerebral performance in the elderly, in improving the sexual behavior of the male old rat with reduction of the latencies and increase of the frequencies of sexual acts.

The compounds may also be used to counteract the excess of oxidative processes, such as those deriving from chronic inflammatory process or by exposures to ionizing radiations.

The acute toxicities by the oral and intraperitoneal routes of the compounds I are very low in mice and rats analogously to PGT; they are higher than 3000 mg/kg.

From what above reported, it is evident that the compounds of formula I may be used in therapy in a number of pathologic conditions such as the treatment of impairments of immune defenses, of autoimmune diseases and of ageing processes.

The invention refers therefore also to pharmaceutical compositions suited for the oral use such as hard or soft gelatin capsules, sugar coated tablets, sachets, drops, syrups, sustained-release forms, injectable formulation, suppositories and the like.

Typically a unit dose will contain from 10 to 500 mg of active principle and the daily dose will depend on several factors but, generally, it will range from 50 to 2000 mg per day. Other active principles may be present the formulations of the invention, which are prepared using conventional carriers, excipients and techniques.

The invention is further illustrated by the following examples.

EXAMPLE 1

3-Pyroglutamyl-thiazolidine-4-carboxamide (I, X=NH$_2$, R=H) (Ia)

4.84 g (0.02 moles) of 3-pyroglutamyl-thiazolidine-4-carboxylic acid are dissolved in 25 ml of DMF; 3.25 g (0.02 moles) of carbonyldiimidazole are added to the solution and this is stirred until no more gas is developed. The thus obtained solution is concentrated under vacuum, ether is added to the residue, the crystalline solid is filtered, dried on calciumchloride and added at 10° C. to a stirred 10% gaseous ammonia solution in methanol. This is stirred for 1 hour, the precipitated crystalline product is filtered and water-crystallized yielding 4.1 g (85) m.p. 239°-240° C. Elemental analysis for C$_9$H$_{13}$N$_3$O$_3$S: Calcd. C%: 44.44, H%: 5.39, N%: 17.28. Found C%: 44.32, H%: 5.25, N%: 16.92.

EXAMPLE 2

N-(3-Pyroglutamyl-thiazolidine-4-carbonyl)morpholine

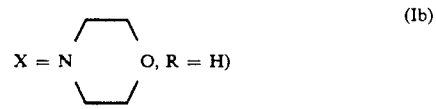

(I, X = N\_\_\_O, R = H) (Ib)

4.84 g (0.02 moles) of 3-pyroglutamyl-thiazolidine-4-carboxylic acid are suspended in 20 ml of DMF and treated with 3.25 g (0.02 mole) of carbonyldiimidazole. After no more gas is developed, 1.72 g (0.02 moles) of morpholine dissolved in 10 ml of DMF is added thereto and shaken for 1 hour. After diluting with 2 volumes of ethyl ether, the solid is filtered and water recrystallized yielding 4.35 g (70%) of product. m.p. 187°-188° C.

Elemental analysis for C$_9$H$_{13}$N$_3$O$_4$S: Calcd. C%: 49.84, H%: 6.11, N%: 13.41. Found C%: 49.86, H%: 5.93, N%: 13.24.

EXAMPLE 3

N-(3-pyroglutamyl-thiazolidine-4-carbonyl)-ethylamine (I, X=NHC$_2$H$_5$, R=H) (Ic)

2.42 g (0.01 moles) of 3-pyroglutamyl-thiazolidine-4-carboxylic acid in 20 ml of DMF is treated with 1.63 g (0.01 moles) carbonyldiimidazole until no more gas is developed.

Ethylamine 0.45 g (0.01 moles) in 70% water solution is added to the above solution and stirred for 1 hour at room temperature.

The solvent is evaporated under vacuum, the oily residue is diluted in acetone, and treated with 4 volumes of ether. The ether-precipitated oil is decanted, diluted with chloroform, loaded in a column containing 50 g of silica and eluted with a mixture of chloroform: methyl alcohol: acetone 80:10:10, collecting 10 ml fractions. The fractions containing the pure product (Rf. 0.7: CHCl$_3$ 50/acetone 20/methyl alcohol 10, iodine detection), are dry-evaporated and the solid residue is crystallized from ethanol yielding 1.7 g (63.2) of product. m.p. 148°-150° C.

Elementary analysis for C$_{11}$H$_{17}$N$_3$O$_3$S: Calcd. C%: 48.65, H%: 6.37, N%: 15.48. Found C%: 48.61, H%: 6.32, N%: 15.63.

The compounds listed in Table 1 are obtained by similar processes.

TABLE 1

[Structure: pyroglutamyl-thiazolidine core with COX-R substituent]

| Compounds | X | R | M.P. | Elemental analysis |
|---|---|---|---|---|
| Id | 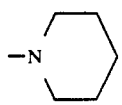 —N | H | 167°–9° C. | in agreement |

TABLE 1-continued

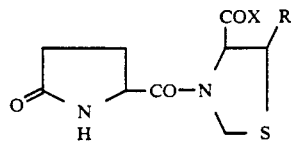

| Compounds | X | R | M.P. | Elemental analysis |
|---|---|---|---|---|
| Ie | -N⟨⟩ (pyrrolidine) | H | 190°-1° C. | " |
| If | -NH-◁ (cyclopropyl) | H | 93°-4° C. | " |
| Ig | $-NHCH_2CH=CH_2$ | H | 76°-7° C. | (1 $H_2O$) in agreement |
| Ih | $-NHCH_2-C_6H_5$ | H | 150°-1° C. | (1 $H_2O$) in agreement |
| Ii | $-NHCH_2-C\equiv CH$ | H | 130°-2° C. | (1 $H_2O$) in agreement |
| Il | $-OC_2H_5$ | H | 82°-3° C. | (1 $H_2O$) in agreement |
| Im | $-N(C_2H_5)_2$ | H | 181°-2° C. | (1 $H_2O$) in agreement |
| In | $-O-CH_2-C_6H_5$ | H | oil, Rf 0.9 | (1 $H_2O$) in agreement |

We claim:

1. A compound of formula I

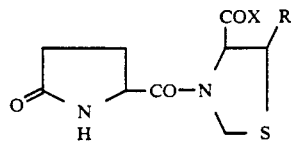

wherein X is a $C_2$-$C_7$ alkoxy or benzyloxy group, an amino group, the residue of a $C_1$-$C_8$ primary or secondary aliphatic amine optionally containing one or more double and/or triple bonds, of a $C_4$-$C_8$ cyclic aliphatic amine optionally containing an oxygen atom and benzylamine; R is hydrogen or $C_1$-$C_8$ alkyl.

2. A compound according to claim 1 wherein X is ethoxy, amino, methylamino, ehtylamino, dimethylamino, diethylamino, cyclopropylamino, allylamino, propargylamino, pyrrolidino, piperidino, morpholino.

3. A compound according to claim 1 wherein R is hydrogen or methyl.

4. A compound according to claim 2 wherein R is hydrogen or methyl.

5. Pharmaceutical compositions capable of stimulating the immune system, which contain as the active principle a compound of claim 1 in admixture with suitable carriers.

6. Pharmaceutical compositions capable of stimulating the immune system, which contain as the active principle a compound of claim 2 in admixture with suitable carriers.

7. Pharmaceutical compositions capable of stimulating the immune system, which contain as the active principle compound of claim 3 in admixture with suitable carriers.

* * * * *